United States Patent
Wade et al.

(10) Patent No.: US 7,879,909 B2
(45) Date of Patent: Feb. 1, 2011

(54) USE OF TREPROSTINIL TO TREAT NEUROPATHIC DIABETIC FOOT ULCERS

(75) Inventors: Michael Wade, Chapel Hill, NC (US); Roger Andrew Jeffs, Chapel Hill, NC (US); Deborah Strootman, Tucson, AZ (US)

(73) Assignee: United Therapeutics Corporation, Silver Spring, MD (US)

( * ) Notice: Subject to any disclaimer, the term of this patent is extended or adjusted under 35 U.S.C. 154(b) by 866 days.

(21) Appl. No.: 11/103,649

(22) Filed: Apr. 12, 2005

(65) Prior Publication Data

US 2005/0282903 A1    Dec. 22, 2005

Related U.S. Application Data

(60) Provisional application No. 60/561,157, filed on Apr. 12, 2004.

(51) Int. Cl.
*A61K 31/557* (2006.01)
(52) U.S. Cl. ..................................... 514/573
(58) Field of Classification Search ................. 514/573
See application file for complete search history.

(56) References Cited

U.S. PATENT DOCUMENTS

| | | | |
|---|---|---|---|
| 4,306,075 A | 12/1981 | Aristoff | |
| 4,490,537 A | 12/1984 | Johnson | |
| 4,499,085 A | 2/1985 | Masuda | |
| 5,153,222 A | 10/1992 | Tadepalli et al. | |
| 5,234,953 A | 8/1993 | Crow et al. | |
| 5,814,301 A | 9/1998 | Klopp et al. | |
| 6,054,486 A * | 4/2000 | Crow et al. | 514/571 |
| 6,171,786 B1 | 1/2001 | Shtil et al. | |
| 6,441,245 B1 | 8/2002 | Moriarty et al. | |
| 6,451,815 B1 | 9/2002 | Hwang et al. | |
| 6,469,022 B1 | 10/2002 | Schellens | |
| 6,521,212 B1 | 2/2003 | Cloutier et al. | |
| 6,528,688 B2 | 3/2003 | Moriarty et al. | |
| 7,417,070 B2 * | 8/2008 | Phares et al. | 514/529 |
| 2005/0085540 A1 | 4/2005 | Phares et al. | |
| 2005/0101608 A1 | 5/2005 | Santel | |
| 2005/0165111 A1* | 7/2005 | Wade et al. | 514/573 |
| 2005/0282901 A1 | 12/2005 | Phares et al. | |
| 2007/0078095 A1 | 4/2007 | Phares et al. | |
| 2007/0078182 A1 | 4/2007 | Phares et al. | |
| 2007/0082948 A1 | 4/2007 | Phares et al. | |

FOREIGN PATENT DOCUMENTS

| | | |
|---|---|---|
| EP | 0 159 784 | 10/1985 |
| WO | WO 99/25357 A1 | 5/1999 |
| WO | WO 00/58303 A1 | 10/2000 |
| WO | WO 2004/019952 A1 | 3/2004 |
| WO | WO 2005/007081 A | 1/2005 |
| WO | WO 2005/058303 A | 6/2005 |

OTHER PUBLICATIONS

Armstrong et al., Diabetic Foot Ulcers:Prevention, Diagnosis and Classification. Am. Fam. Physician. Mar. 15, 1998; 57(6), p. 1325-1332.*
Andros et al. Diagnostic and Therapeutic arterial interventions in the ulcerated diabetic foot. Metab.Res. Rev. 2004 Suppl 1 :S29-33.*
O'Meara et al. (Health Technology Assessment, 2000; 4(21), p. 15-228.*
Fink et al. (Heart Disease (1999), 1: p. 29-40).*
U.S. Appl. No. 60/472,407, filed May 22, 2003, Phares et al.
Clapp et al., "Differential Effects of Stable Prostacyclin Analogs on Smooth Muscle Proliferation and Cyclic AMP Generation in Human Pulmonary Artery," Am. J. Respir. Cell. Mol. Biol., 2002, 26(2):194-201.
Greenhalgh David G., M.D., "Wound healing and diabetes mellitus," Clin. Plast. Surg., 2003, 30:37-45.
Journal of Vascular Surgery, D 4.3 "Pharmacotherapy for Critical Limb Ischemia," Jan. 2000, 31(1)2:S197-S203.
Kantor et al., "Expected Healing Rates for Chronic Wounds," Wounds, Nov./Dec. 2000, 12(6):155-158.
Margolis, et al., "Diabetic Neuropathic Foot Ulcers: The association of the wound size, wound duration and wound healing," Diabetes Care, Oct. 10, 2002, 25(10):1835-39.
Raychaudhuri et al, "The Prostacyclin Analogue Treprositinil Blocks NFκB Nuclear Translocation in Human Alveolar Macrophages," J. Biol. Chem., Sep. 6, 2002, 277(36):33344-33348.

(Continued)

*Primary Examiner*—Yong Chu
*Assistant Examiner*—Valerie Rodriguez-Garcia
(74) *Attorney, Agent, or Firm*—Foley & Lardner LLP

(57) ABSTRACT

The present invention describes novel methods for using 9-deoxy-2',9-α-methano-3-oxa-4,5,6-trinor-3,7-(1',3'-interphenylene)-13,14-dihydro-prostaglandin $F_1$ (also known as Treprostinil) or its derivative, or a pharmaceutically acceptable salt thereof, for the treatment and/or prevention of foot ulcers in subjects with diabetic neuropathy. The invention also relates to kits for treatment and/or prevention of foot ulcers, comprising an effective amount of Treprostinil or its derivative, or a pharmaceutically acceptable salt thereof.

21 Claims, No Drawings

OTHER PUBLICATIONS

Tyle, Praveen, "Iontophoretic Devices for Drug Delivery," Pharmaceutical Research, 1986, 3(6):318-326.

Watkins, Peter J., "ABC of diabetes, The diabetic foot," Brit. Med. J., May 3, 2003, 326:977-979.

Jeffcoate et al., "Diabetic foot ulcers," The Lancet, May 3, 2003, vol. 361, pp. 1545-1551.

Jude et al., "Role of neuropathy and plasma nitric oxide in recurrent neuropathic and neuroischemic diabetic foot ulcers," Wound Repair and Regeneration, Sep. 2001, vol. 9, No. 5, pp. 353-359.

Lee et al., "Efficient In Situ Esterification of Carboxylic Acids Using Cesium Carbonate," Organic Preparations and Procedures International, vol. 28, No. 4, Aug. 1996, pp. 480-483.

Mann et al., Organic Syntheses, John Wiley & Sons, Inc., vol. 75, 1998, pp. 139-145.

Mohler, "Medical Management of Claudication," Up To Date, Inc., Mar. 31, 1997, pp. 1-6.

Mohler, "Clinical Manifestations of Claudication," Up To Date, Inc., Sep. 30, 1996, pp. 1-4.

Neschis et al., "Surgical Indications for the Patient with Limb Threatening Ischemia," pp. 1-10.

Okuda et al., "Acute Effect of Beraprost Sodium on Lower Limb Circulation in Patients with Non-Insulin-Dependent Diabetes Mellitus-Evaluation by Color Doppler Ultrasonography and Laser Cutaneous Blood Flowmetry," Prostaglandins, Elsevier, vol. 52, Nov. 1996, pp. 375-384.

Patterson et al., "Acute Hemodynamic Effects of the Prostacyclin Analog 15AU81 in Service Congestive Heart Failure," The American Journal of Cardiology, vol. 75, Jan. 19, 1995, pp. 26A-33A.

Belch et al., "Randomized, Double-Blind, Placebo-Controlled Study Evaluating the Efficacy and Safety of AS-013, a Prostaglandin $E_1$ Prodrug, in Patients With Intermittent Claudication," Circulation, The American Heart Association, Inc., vol. 95, No. 9, May 1997, pp. 2298-2301.

Chattaraj, Sarat C., "Traprostinil sodium Pharmacia," Current Opinion in Investigational Drugs, Pharmapress, US, Apr. 2002, vol. 3., No. 4, pp. 582-586.

Engel et al., "Treprostinil for the treatment of severe digital necrosis in systemic sclerosis," Vascular Medicine, Feb. 2005, vol. 10, No. 1, pp. 29-32.

Hassner et al., "Direct Room Temperature Esterification of Carboxylic Acids" Tetrahedron Letters, Perganon Press Ltd., vol. 46, 1978, pp. 4475-4478.

Akbari et al., "Diabetes and peripheral vascular disease," J. Vasc. Surg., Aug. 1999, 30(2):373-384.

Armstrong et al., "Diabetic Foot Ulcers: Prevention, Diagnosis and Classification," American Family Physician, Mar. 15, 1998, 57(6):1325-1332.

Baker et al., "Microvascular and C-Fiber Function in Diabetic Charcot Neuroarthropathy and Diabetic Peripheral Neuropathy," Diabetes Care, Dec. 2007, 30(12):3077-3079.

Boulton et al., "Diabetic Neuropathies: A statement by the American Diabetes Association," Diabetes Care, Apr. 2005, 28(4):956-962.

Boulton, Andrew J.M., "Diabetic neuropathy: classification, measurement and treatment," Current Opinion in Endocrinology & Diabetes, 2007, 14:141-145.

La Fontaine et al., "Current Concepts in Diabetic Microvascular Dysfunction," J. Amer. Podiatric Med. Assoc., May/Jun. 2006, 96(3):245-252.

McCarty, M.F., "Nitric oxide deficiency, leukocyte activation and resultant ischemia are crucial to the pathogenesis of diabetic retinopathy/neuropathy—preventive potential of antioxidants, essential fatty acids, chromium, ginkolides, and pentoxifylline," Medical Hypotheses, 1998, 50:435-449.

Norgren et al., "Inter-Society Consensus for the Management of Peripheral Arterial Disease (TASC II)," J. Vasc. Surgery, Jan. 2007, 45(1):Suppl 1:S5A-S67A.

Norgren et al., TASC II Working Group, "Inter-Society Consensus for the Management of Peripheral Arterial Disease (TASC II)," Eur J Vasc Endovasc Surg., 2007, 33 (Suppl 1): S1-75.

Quattrini et al., "Impaired Skin Microvascular Reactivity in Painful Diabetic Neuropathy," Diabetes Care, Mar. 2007, 30(3):655-659.

Rathur et al., "The diabetic foot," Clinics in Dermatology, 2007, 25:109-120.

Rathur et al., "The neuropathic diabetic foot," Nature Clinical Practice, Endocrinology & Metabolism, Jan. 2007, 3(1):14-25.

* cited by examiner

USE OF TREPROSTINIL TO TREAT NEUROPATHIC DIABETIC FOOT ULCERS

CROSS-REFERENCE TO RELATED PATENT APPLICATIONS

The present application claims priority to U.S. provisional patent application No. 60/561,157, filed Apr. 12, 2004, incorporated hereby by reference in its entirety.

BACKGROUND OF THE INVENTION

The invention relates to the use of 9-deoxy-2',9-α-methano-3-oxa-4,5,6-trinor-3,7-(1',3'-interphenylene)-13,14-dihydro-prostaglandin $F_1$ (hereafter "Treprostinil") or its derivative, or a pharmaceutically acceptable salt thereof, to treat foot ulcers, for example, in patients with diabetic neuropathy. This invention also relates to kits to be used for this purpose.

Treprostinil, also known as UT-15, is a known compound disclosed in U.S. Pat. No. 4,306,075 in example 33. Treprostinil is a synthetic analog of epoprostenol, a prostaglandin $F_1$. The activities ascribed to the various compounds of this patent include inhibition of smooth muscle cell proliferation, inhibition of platelet aggregation, inhibition of cytokine secretion, reduction of gastric secretion, vasodialation and bronchodilation.

U.S. Pat. No. 5,153,222 discloses the use of Treprostinil and related compounds to treat pulmonary hypertension. U.S. Pat. No. 6,054,486 discloses the use of Treprostinil and related compounds to treat peripheral vascular disease, such as peripheral arterial occlusive disease and intermittent claudication. Patterson et al., *Amer. J. of Cardiology*, 75: 26A-33A (1995), have shown vasodilator effects of Treprostinil in patients with class III or class IV heart failure.

Clapp et al., *Am. J. Respir. Cell. Mol. Biol.*, 26 (2): 194-201 (2002), have shown that Treprostinil inhibits proliferation of human pulmonary arterial smooth muscle cells. Raychaudhuri et al., *J. Biol. Chem.*, 277 (36): 33344-8 (2002), have disclosed that Treprostinil inhibits inflammatory cytokine (tumor necrosis factor-α, interleukin-1β, interleukin-6, and granulocyte macrophage colony-stimulating factor) secretion and gene expression by human alveolar macrophages.

Approximately 15% of all diabetes patients will develop a foot ulcer at some point in their lives, see, e.g., Jeffcoate, W & Harding, K., 2003. Diabetic Foot Ulcers. The Lancet, 362; 154-51, incorporated hereby by reference in its entirety. There are many pathways for a diabetic foot ulcer to develop. In general, approximately 20% of patients with diabetes will develop a foot ulcer primarily as a result of inadequate arterial blood flow (peripheral arterial disease), 50% from diabetic neuropathy, and 30% from a combination of lower limb ischemia and diabetic neuropathy. Since not all methods suitable for treating ischemic lesions can necessarily be used to treat ulcers caused by diabetic neuropathy, the need exits to identify viable methods, as well as kits, that can be used to prevent and treat such ulcers. See, e.g., Margolis, D. Hoffstad, O, Allen-Taylor, L., and Berlin, J., 2002. Diabetic Neuropathic Foot Ulcers: The association of the wound size, wound duration and wound healing. Diabetes Care 25:1835-39, incorporated hereby by reference in its entirety.

In addition, the differences in healing between a vascular leg ulcer (including the foot) and a diabetic foot ulcer can be found in Kantor J, Margolis D. Expected Healing Rates for Chronic Wounds. Wounds 12 (6):155-158, 2000. For example, in a study with 260 patients with vascular leg ulcers (VLU) and 586 patients with diabetic foot ulcers (DFU), 32% VLU failed to heal after 24 weeks of good ulcer care, while 67% DFU failed to heal after 20 weeks of good ulcer care. Other references distinguishing these different ulcers can be found in Watkins, P., Brit. Med. J., 326:977-979 (2003), TransAtlantic Intersociety Consensus (TASC), J. Vasc. Surgery, v. 31, NI part 2, page S199 (2000), and Greenhalgh D G, Clin. Plast. Surg., 30:37-45 (2003), which are incorporated herein by reference in their entirety.

Diabetic neuropathy is a condition in which nerve damage from diabetes caused decreased sensation in the legs and feet. If a patient develops an open area from pressure or from a cut, the patient may not even feel the sore. Left untreated, the damaged area can develop a diabetic foot ulcer that is susceptible to polymicrobial infection that spreads rapidly and causes overwhelming tissue destruction. This infection process is the main reason for major amputation following ulceration in patients with predominantly neuropathic ulceration. Traditional treatment approaches to foot ulcers include desloughing and debridement, pressure relief (e.g., rest, special footwear and shoe inserts and casting), antibiotic treatment for infection and wound dressing. Although certain types of dressings sometimes can help to aid healing of the lesions, these treatments are often unsuccessful.

Neuropathic diabetic foot ulcers can be extremely painful, debilitating, and heal slowly. Thus, the need exists to identify viable methods, as well as kits, that can be used to prevent and treat such ulcers. The present invention satisfies this need and provides related advantages as well.

SUMMARY OF THE INVENTION

The pathophysiology of diabetic foot ulcers is described as first having neuropathic changes uniquely associated with diabetes mellitus, and microangiopathy. Administration of Treprostinil or its derivatives treats neuropathic diabetic foot ulcers. Treprostinil is well suited for such use because the compound is a stable analogue of prostaglandin, can be used in intravenous administration, is not degraded when it passes through the lungs, and has a long biological half-life.

Accordingly, the present invention provides for the treatment of neuropathic diabetic foot ulcers and/or the treatment of symptoms associated with neuropathic diabetic foot ulcers in a mammal, comprising administering to a mammal in need thereof an effective amount of Treprostinil or a derivative thereof or a pharmaceutically acceptable salt. In one embodiment, Treprostinil or a derivative thereof is administered sufficiently early in a disease state to provide a cytoprotective effect. The present invention also provides for kits for accomplishing this purpose.

DETAILED DESCRIPTION OF THE PREFERRED EMBODIMENTS

The inventors believe that therapies that enhance cutaneous blood flow (i.e., to the skin), by increasing blood flow through smaller vessels and capillaries, are effective in treating and preventing neuropathic diabetic foot ulcers. One type of vascular change that is seen in diabetes patients is nonocculusive microcirculatory dysfunction involving capillaries and arterioles. Thus, structural changes in the microcirculation, including capillary basement membrane thickening and abnormal endothelial function, are associated with patients that have diabetes.

Prostacyclins are small molecules that have been previously shown to cause dilation of large blood vessels, relaxation of smooth muscle, inhibition of smooth muscle proliferation, as well as inhibition of platelet aggregation. Similar actions by Treprostinil at the microvascular level and on capillaries near the skin are believed to help enhance cutaneous blood flow and heal and/or prevent neuropathic diabetic foot ulcers.

Diabetic neuropathic foot ulcers are sometimes characterized as not being associated with pain. A foot pulse is usually present and the ulcer has a punched out appearance. The sore is often on the sole or edge of the foot and calluses are present. Other characteristics of the diabetic neuropathic foot can include a loss of sensation, reflexes, and vibration, AV shunting of the blood flow, dilated veins, dry/warm skin temperature, and skin appearance that is red in color. There typically are bone deformities.

This is in contrast to a diabetic neuroischemic ulcer, which is painful and has an irregular appearance around the margins. A foot pulse is usually absent and the ulcer is commonly on the toes. Calluses are absent or infrequent, blood flow is decreased, veins are collapsed, the skin feels cold and the skin color is pale or cyanosed. There are typically no bony deformities.

The present invention relates to methods for treating and/or preventing neuropathic diabetic foot ulcers comprising administering to a subject, preferably a human being, in need thereof an effective amount of Treprostinil and/or a derivative thereof and/or a pharmaceutically acceptable salt. Suitable derivatives include acid derivatives, pro-drugs, sustained release forms, inhaled forms and oral forms of Treprostinil, including those disclosed in U.S. Pat. No. 6,521,212 and co-pending Ser. No. 60/472,407. In some embodiments, pain and/or other symptoms associated with neuropathic diabetic foot ulcers are reduced, eliminated or prevented upon administration of an effective amount of Treprostinil, and/or its pharmaceutically acceptable salts and derivatives thereof.

The present invention also relates to kits for accomplishing such treatment or prevention of neuropathic diabetic foot ulcers. The invention includes a kit for treatment and/or prevention of foot ulcers in a subject with diabetic neuropathy, comprising (i) an effective amount of Treprostinil, its pharmaceutically acceptable salts, and/or acid derivatives thereof, (ii) one or more pharmaceutically acceptable carriers and/or additives, and (iii) instructions for use in treating and/or preventing neuropathic diabetic foot ulcers.

Unless otherwise specified, the term "a" or "an" used herein shall mean "one or more."

As used herein, the phrase "instructions for use" shall mean any FDA-mandated labeling, instructions, or package inserts that relate to the administration of Treprostinil for the purpose of treating and/or preventing neuropathic diabetic foot ulcers. For example, instructions for use may include, but are not limited to, indications for neuropathic diabetic foot ulcers, indications for specific symptoms associated with neuropathic diabetic foot ulcers, such as pain, that can be ameliorated by Treprostinil, and recommended dosage amounts for subjects suffering from neuropathic diabetic foot ulcers.

The term "acid derivative" is used herein to describe C1-4 alkyl esters and amides, including amides wherein the nitrogen is optionally substituted by one or two C1-4 alkyl groups.

The invention also includes bioprecursors or "pro-drugs" of Treprostinil, that is, compounds which are converted in vivo to Treprostinil or its pharmaceutically active derivatives thereof.

Further aspects of the present invention are concerned with the use of Treprostinil, or a pharmaceutically acceptable salt or acid derivative thereof, in the manufacture of a medicament for treatment or prevention of foot ulcers in subjects with diabetic neuropathy.

The present invention encompasses methods of using Treprostinil sodium, currently marketed under the trade name of REMODULIN®. The FDA has approved Treprostinil sodium for the treatment pulmonary arterial hypertension by injection of dose concentrations of 1.0 mg/mL, 2.5 mg/mL, 5.0 mg/mL and 10.0 mg/mL. The chemical structure formula for Treprostinil sodium is:

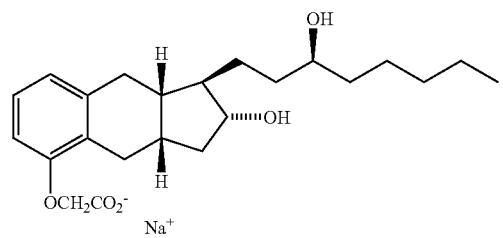

Treprostinil sodium is sometimes designated by the chemical names: (a) [(1R,2R,3aS,9aS)-2,3,3a,4,9,9a-hexahydro-2-hydroxy-1-[(3S)-3-hydroxyoctyl]-1H-benz[f]inden-5-yl]oxy]acetic acid; or (b) 9-deoxy-2',9-α-methano-3-oxa-4,5,6-trinor-3,7-(1',3'-interphenylene)-13,14-dihydro-prostaglandin $F_1$. Treprostinil sodium is also known as: UT-15; LRX-15; 15AU81; UNIPROST™; BW A15AU; and U-62,840. The molecular weight of Treprostinil sodium is 390.52, and its empirical formula is $C_{23}H_{34}O_5$.

The present invention extends to methods of using physiologically acceptable salts of Treprostinil that may be used in the preparation of the pharmacologically active compounds of the invention.

The physiologically acceptable salts of Treprostinil include salts derived from bases. Base salts include ammonium salts, alkali metal salts such as those of sodium and potassium, alkaline earth metal salts such as those of calcium and magnesium, salts with organic bases such as dicyclohexylamine and N-methyl-D-glucamine, and salts with amino acids such as arginine and lysine.

Quaternary ammonium salts can be formed, for example, by reaction with lower alkyl halides, such as methyl, ethyl, propyl, and butyl chlorides, bromides, and iodides, with dialkyl sulphates, with long chain halides, such as decyl, lauryl, myristyl, and stearyl chlorides, bromides, and iodides, and with aralkyl halides, such as benzyl and phenethyl bromides.

The amount of Treprostinil, or a physiologically acceptable salt or acid derivative thereof, which is required in a medication or diagnostic aid according to the invention to achieve the desired effect will depend on a number of factors, such as the specific application, the nature of the particular compound used, the mode of administration, the concentration of the compound used, and the weight and condition of the patient. A daily dose per patient for treatment or prevention of neuropathic diabetic foot ulcers may be in the range 25 µg to 250 mg; 0.5 µg to 2.5 mg, or 7 µg to 285 µg, per day per kilogram bodyweight. For example, an intravenous dose in the range 0.5 µg to 1.5 mg per kilogram bodyweight per day may conveniently be administered as an infusion of from 0.5 ng to 1.0 µg per kilogram bodyweight per minute. One possible dosage is 2.5 ng/kg/min, increased over 12 weeks by an amount of 2.50 ng/kg/min each week, until a target dose, such as 15 ng/kg/min, is reached. Infusion fluids suitable for this purpose contain, for example, from 10 ng to 1 µg per milliliter. Ampoules for injection contain, for example, from 0.1 µg to 1.0 mg and orally administrable unit dose formulations, such as tablets or capsules, contain, for example, from 0.1 to 100 mg, typically from 1 to 50 mg. For diagnostic purposes, a single unit dose formulation may be administered. In the case of physiologically acceptable salts, the weights indicated above refer to the weight of the active compound ion, that is, the ion derived from Treprostinil.

In the manufacture of a medicament or diagnostic aid according to the invention, hereinafter referred to as a "formulation", Treprostinil and its physiologically acceptable salts and acid derivatives may be admixed with, inter alia, an acceptable carrier. The carrier must, of course, be acceptable in the sense of being compatible with any other ingredients in the formulation and must not be deleterious to the subject. The carrier may be a solid or a liquid, or both, and is preferably formulated with the compound as a unit-dose formulation, for example, a tablet, which may contain from 0.05% to 95% by weight of the active compound. One or more of Treprostinil and/or its physiologically acceptable salts or acid derivatives may be incorporated in the formulations of the invention, which may be prepared by any of the well known techniques of pharmacy for admixing the components.

In addition to Treprostinil, other pharmacologically active substances may be present in the formulations of the present invention which are known to be useful for treating and/or preventing foot ulcers in patients with diabetic neuropathy. For example, the compounds of the invention may be present in combination with analgesics to treat pain, dressing changes, vasodilator medications, and topical or oral antibiotics.

The formulations of the invention include those suitable for parenteral (e.g., subcutaneous, intramuscular, intradermal, or intravenous), oral, inhalation (in solid and liquid forms), rectal, topical, buccal (e.g., sub-lingual) and transdermal administration, although the most suitable route in any given case may depend on the nature and severity of the condition being treated and on the nature of the particular form of Treprostinil, as well as the physiologically acceptable salt or acid derivative thereof, which is being used.

Formulations of the present invention suitable for parenteral administration conveniently comprise sterile aqueous preparations of Treprostinil, or a physiologically acceptable salt or acid derivative thereof, where the preparations may be isotonic with the blood of the intended recipient. These preparations may be administered by means of subcutaneous injection, although administration may also be effected intravenously or by means of intramuscular or intradermal injection. Such preparations may conveniently be prepared by admixing the compound with water or a glycine or citrate buffer and rendering the resulting solution sterile and isotonic with the blood. Injectable formulations according to the invention may contain from 0.1 to 5% w/v of active compound and may be administered at a rate of 0.1 ml/min/kg. Alternatively, the invention may administered at a rate of 0.625 to 50 ng/kg/min. Alternatively, the invention may be administered at a rate of 10 to 15 ng/kg/min.

Formulations suitable for oral administration may be presented in discrete units, such as capsules, cachets, lozenges, or tablets, each containing a predetermined amount of Treprostinil or a physiologically acceptable salt or acid derivative thereof; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients).

In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising Treprostinil, or a physiologically acceptable salt or acid derivative thereof, in a flavored base, usually sucrose and acacia or tragacanth; and pastilles comprising the compound in an inert base such as gelatin and glycerin or sucrose and acacia.

Formulations suitable for rectal administration are preferably presented as unit dose suppositories. These may be prepared by admixing Treprostinil, or a physiologically acceptable salt or acid derivative thereof, with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include vaseline, lanoline, polyethylene glycols, alcohols, and combinations of two or more thereof. The active compound is generally present at a concentration of from 0.1 to 15% w/w, for example, from 0.5 to 2% w/w. Formulations for transdermal administration may be delivered by iontophoresis (see, for example, *Pharmaceutical Research*, 3 (6): 318 (1986)) and typically take the form of an optionally buffered aqueous solution of Treprostinil or of a salt or acid derivative thereof. Suitable formulations comprise citrate or bis/tris buffer (pH 6) or ethanol/water and contain from 0.1 to 0.2M active ingredient.

The compounds of the present invention are conveniently prepared by methods the same as or analogous to those described in U.S. Pat. No. 4,306,075, U.S. Pat. No. 6,528,688 and U.S. Pat. No. 6,441,245.

Additional embodiments are within the scope of the invention. For example, in one embodiment, a method for treating and/or preventing a foot ulcer in a subject (such as human being) with diabetic neuropathy comprises administering to a subject in need thereof an effective amount of Treprostinil or its derivative, or a pharmaceutically acceptable salt thereof.

In another embodiment, a kit for treatment and/or prevention of a foot ulcer in a subject with diabetic neuropathy, comprises (i) an effective amount of Treprostinil or its derivative, or a pharmaceutically acceptable salt thereof, (ii) one or more pharmaceutically acceptable carriers and/or additives, and (iii) instructions for use in treating or preventing a foot ulcer in a subject with diabetic neuropathy.

In certain method embodiments, administering to a subject in need thereof an effective amount of Treprostinil or its derivative, or a pharmaceutically acceptable salt thereof results in pain or other symptoms associated with a foot ulcer being reduced, eliminated or prevented.

In certain method embodiments, the Treprostinil or its derivative, or a pharmaceutically acceptable salt thereof, is administered subcutaneously, by continuous subcutaneous infusion, intravenously, in an orally available form selected from the group consisting of tablets and capsules, and/or by inhalation. In other embodiments, the effective amount of Treprostinil or its derivative, or a pharmaceutically acceptable salt thereof, is at least 1.0 ng/kg of body weight/min.

In certain kit embodiments, the Treprostinil or its derivative, or a pharmaceutically acceptable salt thereof, is in a form suitable for subcutaneous administration, continuous subcutaneous infusion, intravenously administration or inhalation. In other kit embodiments, the Treprostinil or its derivative, or a pharmaceutically acceptable salt thereof, is in an orally available form selected from the group consisting of tablets and capsules. In another kit embodiment, the effective amount of Treprostinil or its derivative, or a pharmaceutically acceptable salt thereof, is at least 1.0 ng/kg of body weight/min.

The use of Treprostinil for treating foot ulcers in patients with diabetic neuropathy can be illustrated in more details by the following example, however, it should be understood that the present invention is not limited thereto.

EXAMPLE 1

Treprostinil Sodium (Remodulin®) is Safe and Promotes Ischemic Wound Healing and Relief of Rest Pain in Patients with Diabetes and Peripheral Arterial Disease INTRODUCTION: The purpose of this open-label study is to evaluate the safety and efficacy of treprostinil sodium, a stable prostacyclin analogue, in ten patients with PAD, diabetes and inoperable ischemic foot ulcers.

METHODS: Treprostinil sodium was administered as a continuous subcutaneous infusion beginning at 2.5 ng/Kg/Min and titrated to highest tolerated dose for 12 weeks. Patients were monitored for adverse events, wound healing, skin perfusion pressure and ischemic rest pain.

RESULTS: Seven patients have completed the trial to-date. No serious adverse events attributed to treprostinil occurred during the trial. The only drug related side effect reported was mild to moderate infusion site pain. Two patients experienced complete healing. Two patients experienced partial healing. Five experienced complete resolution of rest pain.

CONCLUSIONS: Treprostinil sodium is safe and has a positive effect on ischemic rest pain, skin perfusion, and wound healing.

EXAMPLE 2

Enhancement of Peri-Wound Oximetric and Laser Doppler Signals with Treprostinil Sodium (Remodulin®) in Ischemic Limbs INTRODUCTION: A case-controlled trial examining the effects of treprostinil sodium (Remodulin®), by continuous subcutaneous infusion, was performed in diabetic patients with recalcitrant lower extremity wounds. The known vasodilator and platelet-aggregation inhibitor properties of treprostinil sodium warranted its evaluation as an adjuvant to wound healing in ischemic extremities. The primary endpoints were wound healing and limb salvage. Amongst the secondary endpoints were resting peri-wound transcutaneous oximetry ($T_cPO_2$) and laser Doppler analysis (LD) and the response of $T_cPO_2$ and LD to an oxygen challenge at ambient or elevated pressure. If treprostinil sodium reduces inflow resistance distal to the pre-capillary sphincter, the $\Delta_pO_2$ between the hypoxic wound center and the inflow blood should increase both in magnitude and in the slope of that difference. This would be the physiologic basis for the augmentation of the hypoxic signal.

METHODS: The seven enrolled patients were diabetics with non-healing wounds present (>3 months) in critically ischemic lower extremities (Fontaine Stage III-IV or Rutherford Stage 4, 5 or 6). The treprostinil sodium (Remodulin®) was given by continuous subcutaneous infusion for the study period of 6 weeks. Candidacy for hyperbaric oxygen treatment was an exclusion criterion (patient refusal, logistical constraints or a recently completed $HBO_2$ course). Hyperbaric oxygen exposures were included as diagnostic/monitoring indices. $T_cPO_2$/LD measurements were made at ambient pressure and at 1, 2.0 or 2.4 atmospheres absolute (ATA) before Remodulin® was begun and at various points during drug infusion.

RESULTS: $T_cPO_2$/LD data show:

1—All patients but one (the individual with no LD/$T_cPO_2$ improvement on Remodulin®) demonstrated healing in wounds with a mean interval of "healing arrest" of 10.5 months.

2—All patients (with exception of one) demonstrated improvement in resting peri-wound $T_cPO_2$ values (↑44 to 176%) and in LD signals (236% increase in thermal stimulation response) on Remodulin®.

3—The slope of the $T_cPO_2$ response to $O_2$-challenge at 1, 2.0 and 2.4 ATA increased 56 to 345%.

CONCLUSIONS: The ability of treprostinil sodium to improve tissue blood flow in chronically ischemic wounds is evident from the elevation in resting peri-wound $T_cPO_2$, the magnification of the $O_2$ challenge response at ambient and elevated pressures and the improvement in the laser Doppler signals. This agent can be another adjunct in the treatment of non-healing, ischemic wounds and is clearly synergistic with the effects of hyperbaric oxygen treatment.

EXAMPLE 3

Administration of Treprostinil to Humans with Diabetic Neuropathy Suffering from Foot Ulcers Diabetic neuropathy patients having at least one ulcer (i.e., small sore or area of tissue gangrene) present on a foot are dosed with increasing amounts of Treprostinil over 12 weeks. The medication is delivered by a small pump that is connected to a catheter placed under the skin. In this manner, increasing dosages of Treprostinil are administered to patients by chronic continuous subcutaneous infusion.

Specifically, a 1.0 mg/mL formulation of Treprostinil sodium (REMODULIN®) is administered subcutaneously using a standard micro-infusion, positive-pressure infusion pump designed for subcutaneous drug delivery (Mini-Med). Patients receive an initial dose of 2.5 ng/kg/min of study drug. If, in a given patient, a dose of 2.5 ng/kg/min is not tolerated (e.g., persistent headache, nausea, emesis, restlessness, anxiety or severe pain at infusion site that cannot be adequately managed by medication or topical treatment), the dose is reduced to 1.25 ng/kg/min. Patients are maintained at 2.5 ng/kg/min (or 1.25 ng/kg/min if 2.5 ng/kg/min is not tolerated) during Week 1. After that, the dose is raised by 2.50 ng/kg/min each week until not tolerated or once a target dose is reached.

Dosing is increased weekly unless not tolerated by the patient. Weekly dose increases do not exceed 2.50 ng/kg/min each. One example of a target dose is 15 ng/kg/min. The minimum dose is usually not less than 0.625 ng/kg/min. After completion of the Week 12 treatment, drug infusion are terminated by gradual reduction of the infusion rate (over a period of 1-4 hours, as clinically indicated) until a rate of 0 ng/kg/min is reached.

Patients receiving the above-described treatment experience fewer new foot ulcers associated with diabetic neuropathy, and see a reduction in the number, size and severity of foot ulcers present before treatment. The administration of Treprostinil treats and prevents foot ulcers in patients with diabetic neuropathy.

It will be apparent to those skilled in the art that various modifications and variations can be made to the compositions and processes of this invention. Thus, it is intended that the present invention cover such modifications and variations, provided they come within the scope of the appended claims and their equivalents.

The disclosure of all publications cited above are expressly incorporated herein by reference in their entireties to the same extent as if each were incorporated by reference individually.

What is claimed is:

1. A method for treating a diabetic neuropathic foot ulcer, comprising administering to a subject with diabetic neuropathy in need thereof an effective amount of Treprostinil or its derivative, or a pharmaceutically acceptable salt thereof, wherein said derivative is a sustained release form of Treprostinil, an inhaled form of Treprostinil, an oral form of Treprostinil or an acid derivative of Treprostinil, wherein the subject has diabetic neuropathy but not peripheral vascular disease.

2. The method of claim 1, wherein said administering results in symptoms associated with the diabetic neuropathic foot ulcer in the subject being reduced or eliminated.

3. The method of claim 1, wherein said administering is administering to the subject an effective amount of a pharmaceutically acceptable salt of Treprostinil.

4. The method of claim 1, wherein the subject is a human being.

5. The method of claim 1, wherein said administering is subcutaneous administering.

6. The method of claim 1, wherein said administering is administering by continuous subcutaneous infusion.

7. The method of claim 1, wherein said administering is intravenous administering.

8. The method of claim 1, wherein said administering is administering in an orally available form selected from the group consisting of tablets and capsules.

9. The method of claim 1, wherein said administering is administering by inhalation.

10. The method of claim 1, wherein the effective amount is at least 1.0 ng/kg of body weight/min.

11. A method for reducing or eliminating a pain associated with or caused by a diabetic neuropathic foot ulcer comprising administering to a subject with diabetic neuropathy in need thereof an effective amount of Treprostinil or its derivative, or a pharmaceutically acceptable salt thereof, wherein said derivative is a sustained release form of Treprostinil, an inhaled form of Treprostinil, an oral form of Treprostinil or an acid derivative of Treprostinil, wherein the subject has diabetic neuropathy but not peripheral vascular disease.

12. The method of claim 11, wherein said administering is administering to the subject an effective amount of a pharmaceutically acceptable salt of Treprostinil.

13. The method of claim 11, wherein the subject is a human being.

14. The method of claim 11, wherein said administering is subcutaneous administration.

15. The method of claim 11, wherein said administering is administering by continuous subcutaneous infusion.

16. The method of claim 11, wherein said administering is intravenous administering.

17. The method of claim 11, wherein said administering is administering in an orally available form selected from the group consisting of tablets and capsules.

18. The method of claim 11, wherein said administering is administering by inhalation.

19. The method of claim 11, wherein the effective amount is at least 1.0 ng/kg of body weight/min.

20. The method of claim 1, wherein said administering comprises orally administering to the subject an oral formulation comprising diethanolamine salt of treprostinil.

21. The method of claim 11, wherein said administering comprises orally administering to the subject an oral formulation comprising diethanolamine salt of treprostinil.

* * * * *